(12) United States Patent
Kawada et al.

(10) Patent No.: US 9,512,131 B2
(45) Date of Patent: Dec. 6, 2016

(54) ORGANIC SEMICONDUCTOR MATERIAL FOR ORGANIC TRANSISTOR, AND ORGANIC TRANSISTOR ELEMENT

(71) Applicant: NIPPON STEEL & SUMIKIN CHEMICAL CO., LTD., Tokyo (JP)

(72) Inventors: Atsushi Kawada, Kitakyushu (JP); Takuo Nagahama, Kitakyushu (JP); Hiroyuki Hayashida, Kitakyushu (JP); Kouta Masutani, Kitakyushu (JP)

(73) Assignee: NIPPON STEEL & SUMIKIN CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 14/780,380

(22) PCT Filed: Feb. 12, 2014

(86) PCT No.: PCT/JP2014/053119
§ 371 (c)(1),
(2) Date: Sep. 25, 2015

(87) PCT Pub. No.: WO2014/156342
PCT Pub. Date: Oct. 2, 2014

(65) Prior Publication Data
US 2016/0049594 A1    Feb. 18, 2016

(30) Foreign Application Priority Data
Mar. 28, 2013   (JP) ................. 2013-068752

(51) Int. Cl.
| | | |
|---|---|---|
| *C07D 487/04* | (2006.01) | |
| *H01L 51/00* | (2006.01) | |
| *C07D 519/00* | (2006.01) | |
| *H01L 51/05* | (2006.01) | |

(52) U.S. Cl.
CPC ......... *C07D 487/04* (2013.01); *H01L 51/0072* (2013.01); *C07D 519/00* (2013.01); *H01L 51/0558* (2013.01)

(58) Field of Classification Search
CPC .................................................. C07D 487/04
See application file for complete search history.

(56) References Cited

U.S. PATENT DOCUMENTS

| | | |
|---|---|---|
| 7,456,424 B2 | 11/2008 | Wu et al. |
| 2005/0258417 A1 | 11/2005 | Minakata |
| 2011/0253944 A1* | 10/2011 | Han .............. C07D 209/02 252/500 |

FOREIGN PATENT DOCUMENTS

| | | |
|---|---|---|
| JP | 2012-513459 A | 6/2012 |
| JP | 2012-520872 A | 9/2012 |
| WO | WO 03/016599 A1 | 2/2003 |

OTHER PUBLICATIONS

Xing et al. Chem. Eur. J. 2013, 19, 12788-12793.*
Anthony et al., "A Road Map to Stable, Soluble, Easily Crystallized Pentacene Derivatives," Organic Letters (2002), vol. 4, No. 1, pp. 15-18.
Boudreault et al., "New indolo[3,2-b]carbazole derivatives for field-effect transistor applications," J. Mater. Chem. (2009), vol. 19, pp. 2921-2928.
Boudreault et al., "Synthesis, Characterization, and Application of Indolo[3,2,-b]carbazole Semiconductors," J. Am. Chem. Soc. (2007), vol. 129, pp. 9125-9136.
English translation of International Preliminary Report on Patentability and Written Opinion issued Sep. 29, 2015, in PCT International Application No. PCT/JP2014/053119.
Klauk et al., "High-mobility polymer gate dielectric pentacene tin flim transistors," J. Appl. Phys. (Nov. 1, 2002), vol. 92, No. 9, pp. 5259-5263.
Sirringhaus et al., "Integrated Optoelectronic Devices Based on Conjugated Polymers," Science (Jun. 12, 1998), vol. 280, pp. 1741-1744.
Sundar et al., "Elastomeric Transistor Stamps: Reversible Probing of Charge Transport in Organic Crystals," Science (Mar. 12, 2004), vol. 303, pp. 1644-1646.
Xiao et al., "A Highly π-stacked Organic Semiconductor for Field-Effect Transistors Based on Linearly Condensed Pentathienoacene," J. Am.Chem. Soc. (2005), vol. 127, pp. 13281-13286.

* cited by examiner

*Primary Examiner* — Matthew Coughlin
(74) *Attorney, Agent, or Firm* — Birch, Stewart, Kolasch & Birch, LLP

(57) ABSTRACT

Provided are a semiconductor material for an organic transistor having a high charge mobility, solvent solubility, oxidation stability, and satisfactory film formability, and an organic thin-film transistor using the semiconductor material. The organic semiconductor material for an organic transistor is a seven-ring-fused heterocyclic compound having benzene rings at both ends, and having, therebetween, rings of a structure in which benzene rings A and pyrrole rings B are fused in the order of A-B-A-B-A. The fused heterocyclic compound may be substituted with an alkyl group, an alkenyl group, an alkynyl group, or an aromatic group. In addition, the organic thin-film transistor includes a semiconductor layer using the compound.

3 Claims, 2 Drawing Sheets

ORGANIC SEMICONDUCTOR MATERIAL FOR ORGANIC TRANSISTOR, AND ORGANIC TRANSISTOR ELEMENT

TECHNICAL FIELD

The present invention relates to an organic semiconductor material for an organic transistor, and an organic transistor device.

BACKGROUND ART

In general, a high-temperature process and a high-vacuum process are essential for the formation of a semiconductor device using silicon, which is an inorganic semiconductor material, into a thin film. The high-temperature process is needed and hence silicon cannot be formed into a thin film on a plastic substrate or the like. Accordingly, it has been difficult to impart flexibility to a product into which the semiconductor device is incorporated or to reduce the weight of the product. In addition, the high-vacuum process is needed, and hence an increase in area of the product into which the semiconductor device is incorporated and a reduction in cost of the product have been difficult.

Under such circumstances, in recent years, research has been conducted on an organic semiconductor device utilizing an organic semiconductor material as an organic electronic part (such as an organic electroluminescence (EL) device, an organic thin-film transistor device, or an organic thin-film photoelectric conversion device). Such organic semiconductor material can markedly reduce a production process temperature as compared to the inorganic semiconductor material, and hence can be formed into a thin film on the plastic substrate or the like. Further, when an organic semiconductor having high solubility in a solvent and having satisfactory film formability is used, a thin film can be formed by an application method which does not require a vacuum process, for example, with an inkjet apparatus or the like. Consequently, the increase in area and the reduction in cost, which have been difficult in the case of the semiconductor device using silicon, which is the inorganic semiconductor material, are expected to be realized. As described above, the organic semiconductor material has advantages in, for example, the increase in area, the flexibility, the reduction in weight, and the reduction in cost as compared to the inorganic semiconductor material. Accordingly, the organic semiconductor material has been expected to find applications in organic semiconductor products taking advantage of such characteristics, e.g., information tags, large-area sensors such as electronic artificial skin sheets and sheet-type scanners, and displays such as liquid crystal displays, electronic paper, and organic EL panels.

The organic semiconductor material to be used for the organic semiconductor device expected to find a wide range of applications as described above is required to have a high charge mobility. For example, in an organic transistor, the charge mobility directly affects a switching speed and performance of an apparatus to be driven, and hence an improvement in charge mobility is an essential issue in achieving practical use. Further, as described above, in order to enable production of a semiconductor device by the application method, the organic semiconductor material is required to have solvent solubility, oxidation stability, and satisfactory film formability.

The high charge mobility is particularly mentioned as a characteristic required of the organic semiconductor. From this viewpoint, an organic semiconductor material having a charge-transporting property comparable to that of amorphous silicon has been reported in recent years. For example, the same level of charge mobility as that of the amorphous silicon has been reported in an organic field-effect transistor device (OFET) using, as an organic semiconductor material, pentacene, which is a hydrocarbon-based acene-type polycyclic aromatic molecule in which five benzene rings are linearly fused (Non Patent Literature 1). However, the use of pentacene as an organic semiconductor material for an OFET is disadvantageous from the viewpoints of an increase in area, flexibility, a reduction in weight, and a reduction in cost because an organic semiconductor thin-film layer is formed by a deposition method in an ultrahigh vacuum. In addition, there has been proposed a method of forming a pentacene crystal in a dilute solution of trichlorobenzene without employing a vacuum deposition method, but the production method is difficult and hence a stable device has not been obtained yet (Patent Literature 1). The fact that the hydrocarbon-based acene-type polycyclic aromatic molecule like pentacene has low oxidation stability has also been pointed out as a problem.

In addition, a polythiophene derivative having a long-chain alkyl group, such as poly(3-hexylthiophene), is soluble in a solvent, and its use in production of an organic semiconductor device by the application method has been reported. However, there has been a problem in that its charge mobility is lower than that of a crystalline compound, and hence characteristics of the resultant organic semiconductor device are low (Non Patent Literature 2).

In addition, pentathienoacene, in which thiophene rings are fused, is improved in oxidation resistance as compared to pentacene. However, pentathienoacene has a low carrier mobility and requires many steps in its synthesis, and hence has not been a material preferred for practical use (Non Patent Literature 3).

In addition, recently, there has been a report of an extremely high mobility achieved with a single crystal of rubrene, which is an acene having high solubility. However, a film of rubrene formed by solution casting does not adopt such single-crystal structure, and does not provide a sufficient mobility (Non Patent Literature 4).

As examples of a hydrocarbon-based acene-type compound having high solvent solubility and being relatively stable against oxidation, some compounds each obtained by substituting the 6- and 13-positions of pentacene with silylethynyl groups have been reported to provide coating films having good stability (Non Patent Literature 5). However, in such report, a qualitative property, i.e. an improvement in stability against oxidation is only mentioned, and stability sufficient for practical use has not yet been obtained.

Meanwhile, a heteroacene-based skeleton obtained by introducing a heteroatom, such as nitrogen or sulfur, into a hydrocarbon-based acene-type polycyclic aromatic skeleton has recently been reported. However, its characteristics are not sufficient, and for example, in the case of an indolocarbazole-based material obtained by introducing nitrogen as the heteroatom, a sufficient charge mobility has not yet been obtained (Patent Literature 2).

CITATION LIST

Patent Literature

[PTL 1] WO 2003/016599 A1
[PTL 2] U.S. Pat. No. 7,456,424 A1

Non Patent Literature

[NPL 1] Journal of Applied Physics, Vol. 92, 5259 (2002)
[NPL 2] Science, Vol. 280, (5370) 1741 (1998)

[NPL 3] Journal of American Chemical Society, Vol. 127, 13281 (2005)
[NPL 4] Science, Vol. 303 (5664), 1644 (2004)
[NPL 5] Org. Lett., Vol. 4, 15 (2002)

SUMMARY OF INVENTION

An object of the present invention is to provide an organic semiconductor material for an organic transistor having a high charge mobility, oxidation stability, and solvent solubility, and an organic transistor using the organic semiconductor material.

The inventors of the present invention have made extensive investigations. As a result, the inventors have found an organic semiconductor material having a high charge mobility, oxidation stability, and solvent solubility, and have found that an organic transistor having high characteristics is obtained through the use of the organic semiconductor material in an organic transistor device. Thus, the inventors have attained the present invention.

According to one embodiment of the present invention, there is provided an organic semiconductor material for an organic transistor, including a compound represented by the following general formula (1).

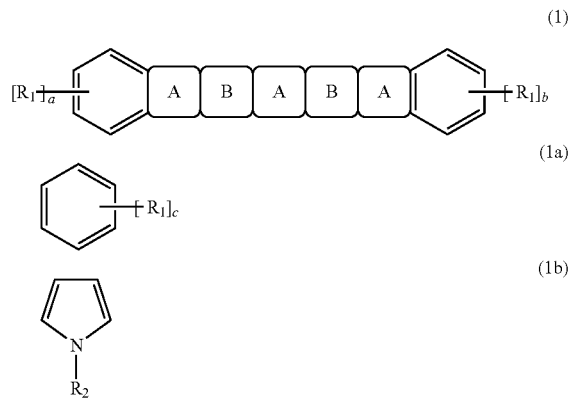

Wherein, rings A each represent an aromatic ring represented by the formula (1a) to be fused to adjacent rings at arbitrary positions; rings B each represent a heterocycle represented by the formula (1b) to be fused to adjacent rings at arbitrary positions; $R_1$'s each independently represent a group selected from the group consisting of an alkyl group having 1 to 30 carbon atoms, an aromatic hydrocarbon group having 6 to 50 carbon atoms, a heteroaromatic group having 3 to 50 carbon atoms, an alkenyl group having 2 to 50 carbon atoms, and an alkynyl group having 2 to 50 carbon atoms; $R_2$'s each independently represent a group selected from the group consisting of hydrogen, an alkyl group having 1 to 30 carbon atoms, an aromatic hydrocarbon group having 6 to 50 carbon atoms, and a heteroaromatic group having 3 to 50 carbon atoms; and a, b, and c each represent an integer of 0 or more satisfying a relationship of a+b+c≥0.

In preferred embodiments, in the general formula (1), a+b+c is an integer of 1 or more and at least one of $R_1$'s represents a group selected from the group consisting of an alkenyl group having 2 to 50 carbon atoms and an alkynyl group having 2 to 50 carbon atoms.

According to another embodiment of the present invention, there is provided a production method for the organic semiconductor material for an organic transistor, the production method including allowing a compound represented by the following general formula (2) and a compound represented by the following general formula (3) to react with each other to produce a compound in which X in the general formula (2) is substituted with $R_1$.

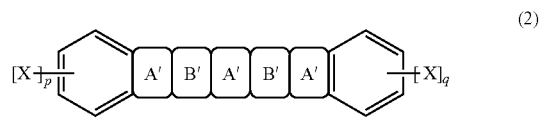

Wherein, rings A' each represent an aromatic ring represented by the formula (2a) to be fused to adjacent rings at arbitrary positions; rings B' each represent a heterocycle represented by the formula (2b) to be fused to adjacent rings at arbitrary positions; X represents any one of a halogen atom, a $CF_3SO_3$ group, a trialkylsilyl group, an organoboron group, an organotin group, a magnesium halide group, and a zinc halide group; and p, q, and r each represent an integer of 0 or more satisfying a relationship of p+q+r≥1.

$$R_1\text{—}Y \quad (3)$$

Wherein, $R_1$ has the same meaning as $R_1$ in the general formula (1); and Y represents a group which reacts with X in the general formula (2) to leave as X—Y and to allow substitution of X with $R_1$.

The organic semiconductor material of the present invention has a high charge mobility characteristic. Therefore, an organic thin-film transistor of the present invention can express high characteristics, and consequently, an organic transistor having high characteristics can be obtained. Accordingly, the technical value of the organic semiconductor material of the present invention is high.

DESCRIPTION OF EMBODIMENTS

Figure 1:
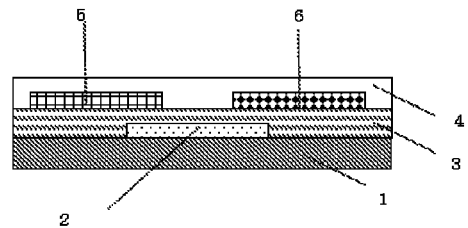
FIG. 1 is a schematic sectional view for illustrating an example of an organic field-effect transistor device.

An organic semiconductor material of the present invention is a compound represented by the general formula (1).
The skeleton of the compound represented by the general formula (1) has a structure in which a plurality of benzene rings, a plurality of rings A, and a plurality of rings B are fused. Therefore, the skeleton represented by the general formula (1) has isomers represented by the following general formulae (4) to (17).
-continued
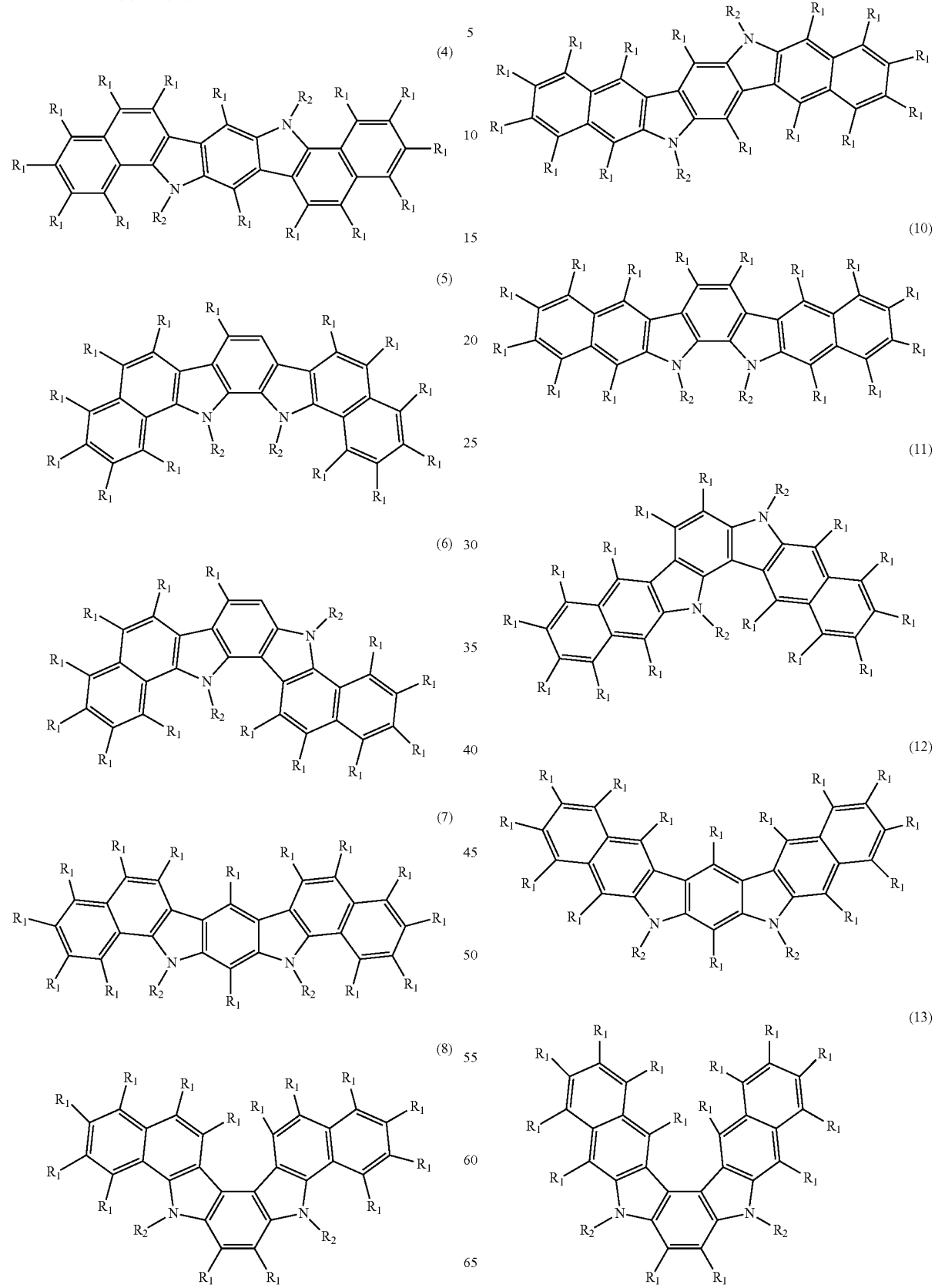

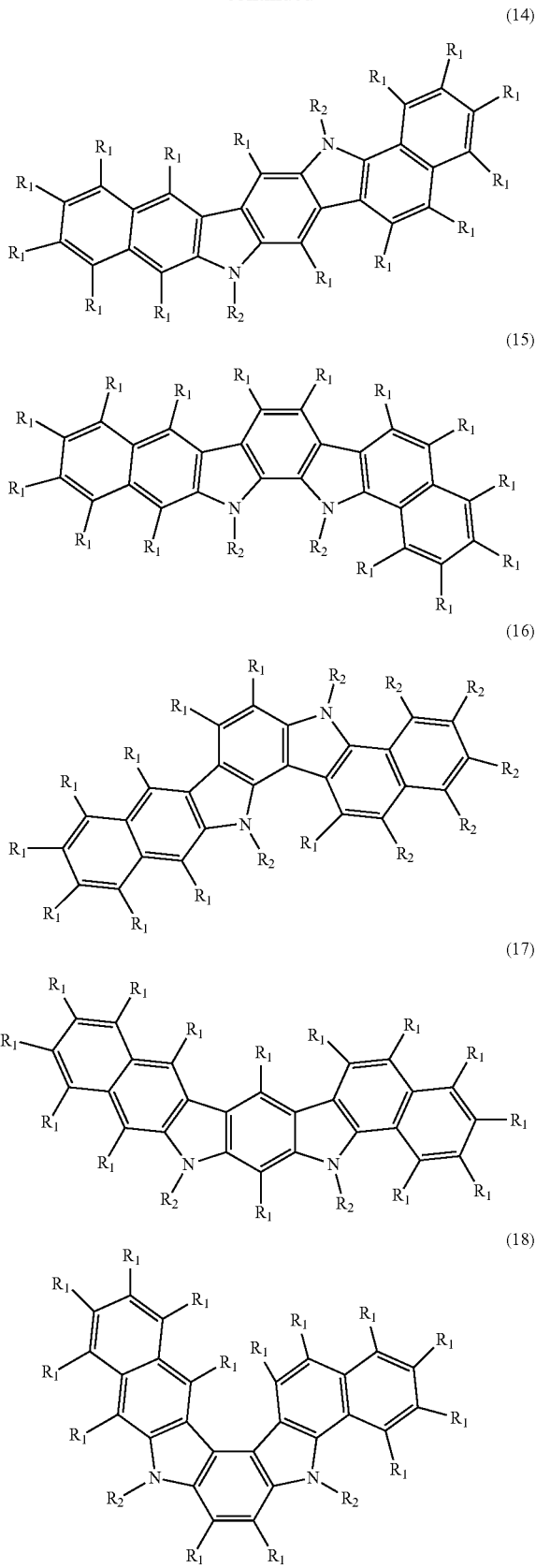

In the general formula (1) (meant to include the formulae (1a) and (1b) unless otherwise stated), the rings A each represent an aromatic ring represented by the formula (1a) to be fused to adjacent rings, and the rings B each represent a heterocycle represented by the formula (1b) to be fused to adjacent rings. $R_1$'s in the general formula (1) and the formula (1a) each independently represent a group selected from the group consisting of an alkyl group having 1 to 30 carbon atoms, an aromatic hydrocarbon group having 6 to 50 carbon atoms, a heteroaromatic group having 3 to 50 carbon atoms, an alkenyl group having 2 to 50 carbon atoms, and an alkynyl group having 2 to 50 carbon atoms. The alkyl group, the aromatic hydrocarbon group, the heteroaromatic group, the alkenyl group, and the alkynyl group may each have a substituent, and when any such group has one or more substituents, the numbers of carbon atoms of the substituents are included in the calculation of the number of carbon atoms of the group.

In the case where $R_1$ represents an alkyl group, preferred examples of the alkyl group may include: linear saturated hydrocarbon groups, such as a n-butyl group, a n-pentyl group, a n-hexyl group, a n-octyl group, a n-dodecyl group, a n-tetradecyl group, a n-octadecyl group, a n-docosyl group, and a n-tetracosyl group; branched saturated hydrocarbon groups, such as an isobutyl group, a neopentyl group, a 2-ethylhexyl group, a 2-hexyloctyl group, and a 4-decyldodecyl group; and saturated alicyclic hydrocarbon groups, such as an alkyl group, a cyclopentyl group, a cyclohexyl group, a cyclooctyl group, a 4-butylcyclohexyl group, and a 4-dodecylcyclohexyl group. The number of carbon atoms of the alkyl group is preferably from 1 to 6.

Preferred examples of the aromatic hydrocarbon group include benzene, pentalene, indene, naphthalene, azulene, heptalene, octalene, indacene, acenaphthylene, phenalene, phenanthrene, anthracene, trindene, fluoranthene, acephenanthrylene, aceanthrylene, triphenylene, pyrene, chrysene, tetraphene, tetracene, pleiadene, picene, perylene, pentaphene, pentacene, tetraphenylene, helicene, hexaphene, rubicene, coronene, trinaphthylene, heptaphene, pyranthrene, ovalene, corannulene, fulminene, anthanthrene, zethrene, terrylene, naphthacenonaphthacene, truxene, and a group produced by removing hydrogen from an aromatic compound in which a plurality of such aromatic rings are linked to each other. More preferred examples of the aromatic hydrocarbon group include benzene, naphthalene, phenanthrene, anthracene, chrysene, and a group produced by removing hydrogen from an aromatic compound in which a plurality of such aromatic rings are linked to each other. The number of carbon atoms of the aromatic hydrocarbon group is preferably from 6 to 24.

Preferred examples of the heteroaromatic group include furan, benzofuran, isobenzofuran, xanthene, oxanthrene, dibenzofuran, peri-xanthenoxanthene, thiophene, thienothiophene, thioxanthene, thianthrene, phenoxathiin, thionaphthene, isothianaphthene, thiophthene, thiophanthrene, dibenzothiophene, pyrrole, pyrazole, tellurazole, selenazole, thiazole, isothiazole, oxazole, furazan, pyridine, pyrazine, pyrimidine, pyridazine, triazine, indolizine, indole, isoindole, indazole, purine, quinolizine, isoquinoline, carbazole, imidazole, naphthyridine, phthalazine, quinazoline, benzodiazepine, quinoxaline, cinnoline, quinoline, pteridine, phenanthridine, acridine, perimidine, phenanthroline, phenazine, carboline, phenotellurazine, phenoselenazine, phenothiazine, phenoxazine, anthyridine, thebenidine, quindoline, quinindoline, acrindoline, phthaloperine, triphenodithiazine, triphenodioxazine, phenanthrazine, anthrazine, benzothiazole, benzimidazole, benzoxazole, benzisoxazole, benzisothiazole, benzodithiophene, naphthodithiophene, anthradithiophene, benzothienobenzothiophene, and a group produced by removing hydrogen from an aromatic compound in which a plurality of such aromatic rings are linked to each other. In addition, a group (group I) produced by removing hydrogen from the compound represented by the general formula (1) may also be used. More preferred examples of the heteroaromatic group include furan, thiophene, thienothiophene, pyrrole, benzodithiophene, naphthodithiophene, anthradithiophene, benzothienobenzothiophene, and a group produced by removing hydrogen from the compound represented by the general formula (1) or an aromatic compound in which a plurality of such aromatic rings are linked to each other. The number of carbon atoms of the heteroaromatic group is preferably from 3 to 24. In addition, the number of the groups I is preferably 0, 1, or 2.

It should be noted that in the case of the group produced from an aromatic compound in which a plurality of aromatic rings are linked to each other, the number of the aromatic rings to be linked to each other is preferably from 2 to 10, more preferably from 2 to 7, and the aromatic rings to be linked to each other may be identical to or different from each other. Herein, the term "aromatic ring" means an aromatic hydrocarbon ring, an aromatic heterocycle, or both which may have a substituent. The term "aromatic group" also has a similar meaning.

Herein, the group produced by linking a plurality of aromatic groups to each other is represented by, for example, any one of the following formulae:

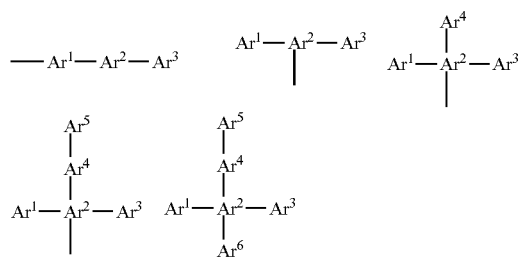

wherein, $Ar^1$ to $Ar^6$ each represent a substituted or unsubstituted aromatic ring.

Specific examples of the group produced by linking a plurality of aromatic groups to each other include groups each produced by removing hydrogen from biphenyl, terphenyl, bipyridine, bipyrimidine, phenylnaphthalene, diphenylnaphthalene, phenylphenanthrene, pyridylbenzene, pyridylphenanthrene, phenylindolocarbazole, dithiophene, terthiophene, thiophenylthienothiophene, or the like.

The alkyl group or the aromatic group may have a substituent, and the substituent is not limited as long as the performance of the semiconductor material is not impaired. The total number of substituents is from 1 to 4, preferably 1 or 2. It should be noted that the group produced from an aromatic compound in which a plurality of aromatic rings are linked to each other may similarly have a substituent. Preferred examples of the substituents of those groups include an alkyl group having 1 to 20 carbon atoms, an alkoxy group having 1 to 20 carbon atoms, an alkylthio group having 1 to 20 carbon atoms, an alkenyl group having 2 to 10 carbon atoms, an alkynyl group having 2 to 10 carbon atoms, an alkoxycarbonyl group having 2 to 10 carbon atoms, an alkylsulfonyl group having 1 to 10 carbon atoms, a haloalkyl group having 1 to 10 carbon atoms, an alkylamide group having 2 to 10 carbon atoms, a trialkylsilyl group having 3 to 20 carbon atoms, a trialkylsilylalkyl group having 4 to 20 carbon atoms, a trialkylsilylalkenyl group having 5 to 20 carbon atoms, and a trialkylsilylalkynyl group having 5 to 20 carbon atoms. More preferred examples of the substituents may include: linear saturated hydrocarbon groups, such as a methyl group, an ethyl group, a n-propyl group, an i-propyl group, a n-butyl group, a n-pentyl group, a n-hexyl group, a n-octyl group, a n-dodecyl group, a n-tetradecyl group, a n-octadecyl group, a n-docosyl group, and a n-tetracosyl group; branched saturated hydrocarbon groups, such as an isobutyl group, a neopentyl group, a 2-ethylhexyl group, a 2-hexyloctyl group, and a 4-decyldodecyl group; saturated alicyclic hydrocarbon groups, such as a cyclopentyl group, a cyclohexyl group, a cyclooctyl group, a 4-butylcyclohexyl group, and a 4-dodecylcyclohexyl group; and a methoxy group, an ethoxy group, a n-propoxy group, an i-propoxy group, and a n-hexyloxy group. When two or more substituents are present, the substituents may be identical to or different from each other.

When $R_1$ represents an alkenyl group, a substituted or unsubstituted alkenyl group having 2 to 50, preferably 2 to 10 carbon atoms may be used. As its substituent, an alkyl group, an aromatic hydrocarbon group, a heteroaromatic group, or an alkylsilyl group may be used. As the alkyl group, the aromatic hydrocarbon group, and the heteroaromatic group, those exemplified above for $R_1$ may be used.

When $R_1$ represents an alkynyl group, a substituted or unsubstituted alkenyl group having 2 to 50, preferably 2 to 10 carbon atoms may be used. As its substituent, an alkyl group, an aromatic hydrocarbon group, a heteroaromatic group, or an alkylsilyl group may be used. As the alkyl group, the aromatic hydrocarbon group, and the heteroaromatic group, those exemplified above for $R_1$ may be used.

In the general formula (1), a and b each represent an integer of from 0 to 4, c represents an integer of from 0 to 2, and a+b+c is an integer of 0 or more. Therefore, the number of $R_1$'s may be 0. However, in order to improve performance as an organic semiconductor material for an organic transistor, a+b+c is preferably 1 or more, more preferably an integer of from 1 to 4, still more preferably 2. When two or more $R_1$'s are present, $R_1$'s may be identical to or different from each other.

It is preferred that the compound represented by the general formula (1) have, as $R_1$'s, one or more, more preferably one to four, still more preferably two alkynyl groups or alkenyl groups each having 2 to 50 carbon atoms. When two or more $R_1$'s are present, the compound may contain both an alkynyl group and an alkenyl group as $R_1$'s.

$R_2$'s in the formula (1b) each independently represent a group selected from hydrogen, an alkyl group having 1 to 30 carbon atoms, an aromatic hydrocarbon group having 6 to 50 carbon atoms, and a heteroaromatic group having 3 to 50 carbon atoms. The alkyl group, the aromatic hydrocarbon group, and the heteroaromatic group may each have a substituent, and when any such group has one or more substituents, the numbers of carbon atoms of the substituents are included in the calculation of the number of carbon atoms of the group. When $R_2$ represents an alkyl group having 1 to 30 carbon atoms, an aromatic hydrocarbon group having 6 to 50 carbon atoms, or a heteroaromatic group having 3 to 50 carbon atoms, the group may be a similar alkyl group, aromatic hydrocarbon group, or heteroaromatic group to that described for $R_1$.

The compound represented by the general formula (1), the compound having $R_1$, may be synthesized by combining known synthesis methods. In the synthesis, it is preferred to allow a compound represented by the general formula (2) and a compound represented by the general formula (3) to react with each other.

In the general formula (2) (meant to include the formulae (2a) and (2b) unless otherwise stated), X represents any one of a halogen atom, a $CF_3SO_3$ group, a trialkylsilyl group, an organoboron group, an organotin group, a magnesium halide group, and a zinc halide group. In the general formula (3), Y represents a group which reacts with X in the general formula (2) to allow substitution of X with $R_1$. In this reaction, X—Y leaves and the position in the general formula (2) at which X has been present is substituted with $R_1$. In the general formulae (2) and (3), the same symbols as those in the general formula (1) have the same meanings as in the general formula (1). Rings A', rings B', p, q, and r are understood to correspond to the rings A, the rings B, a, b, and c of the general formula (1), respectively.

For example, the synthesis may be performed in accordance with the following reaction formula (A), (B), (C), or (D). The compound represented by the general formula (2) is obtained as an intermediate during the synthesis. In addition, other isomers may also be synthesized through the use of their respective corresponding raw materials.

(A)

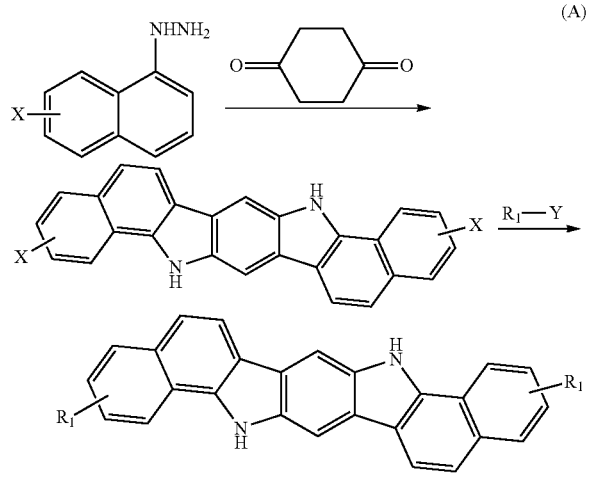

That is, the reaction formula (A) is a method involving allowing 1-naphthylhydrazine having a substituent and 1,4-cyclohexanedione to act to synthesize a skeleton, and then introducing a desired substituent through a substitution reaction with $R_1$—Y. In this case, when 1-naphthylhydrazine having, as the substituent, the same kind of group as X in the general formula (2) is used as a raw material, a compound in which the above-mentioned position in the general formula (2) is substituted with X is obtained as an intermediate, and then, through a substitution reaction with $R_1$—Y, a desired compound represented by the general formula (3) may be obtained. In addition, when 1-naphthylhydrazine having the same kind of group as $R_1$ in the general formula (1) is used, a compound in which the above-mentioned position in the general formula (1) is substituted with $R_1$ may be obtained.

(B)

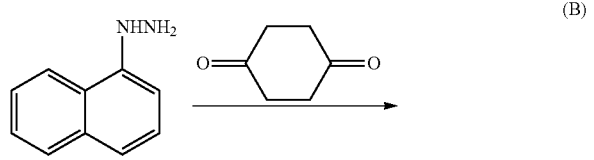

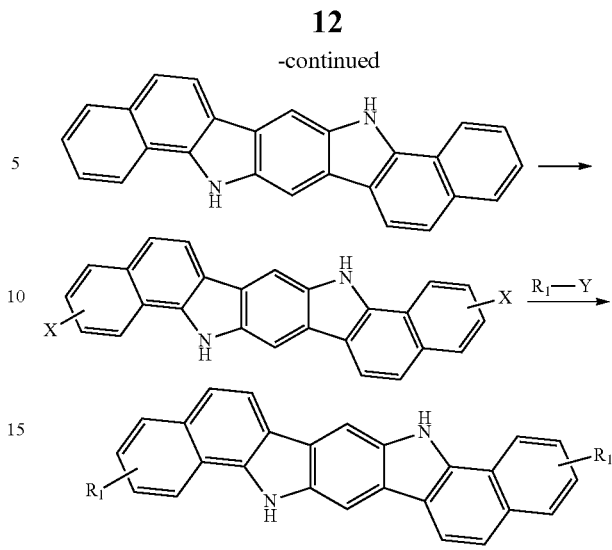

That is, the reaction formula (B) is a method involving allowing 1-naphthylhydrazine and 1,4-cyclohexanedione to act to synthesize a skeleton, and then introducing X, followed by introducing a desired substituent through a substitution reaction with $R_1$—Y.

(C)

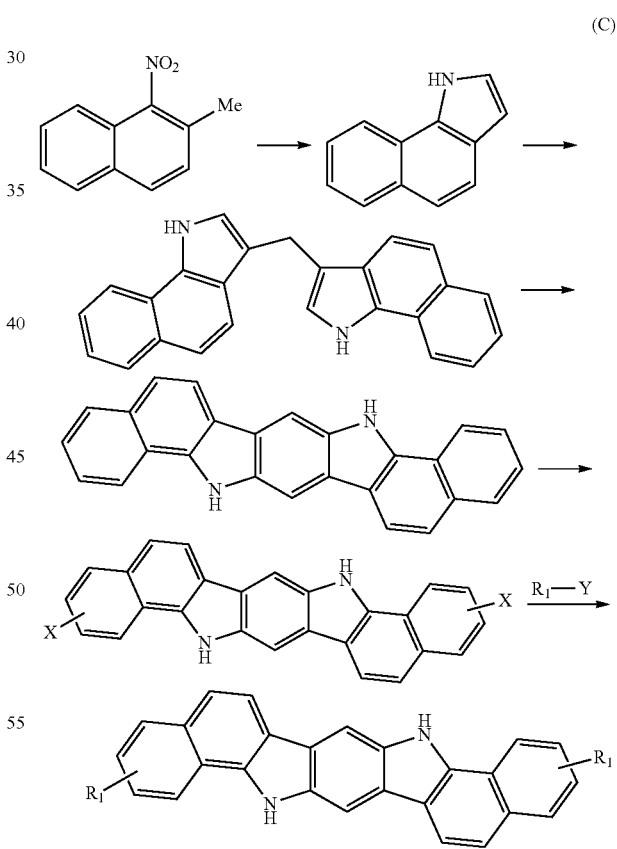

That is, the reaction formula (C) is a method involving obtaining naphthopyrrole from nitromethylnaphthalene, and then performing its dimerization reaction to obtain bisnaphthopyrrolylmethane, followed by an intramolecular cyclization reaction, the introduction of X, and a substitution reaction with $R_1$—Y.

(D)

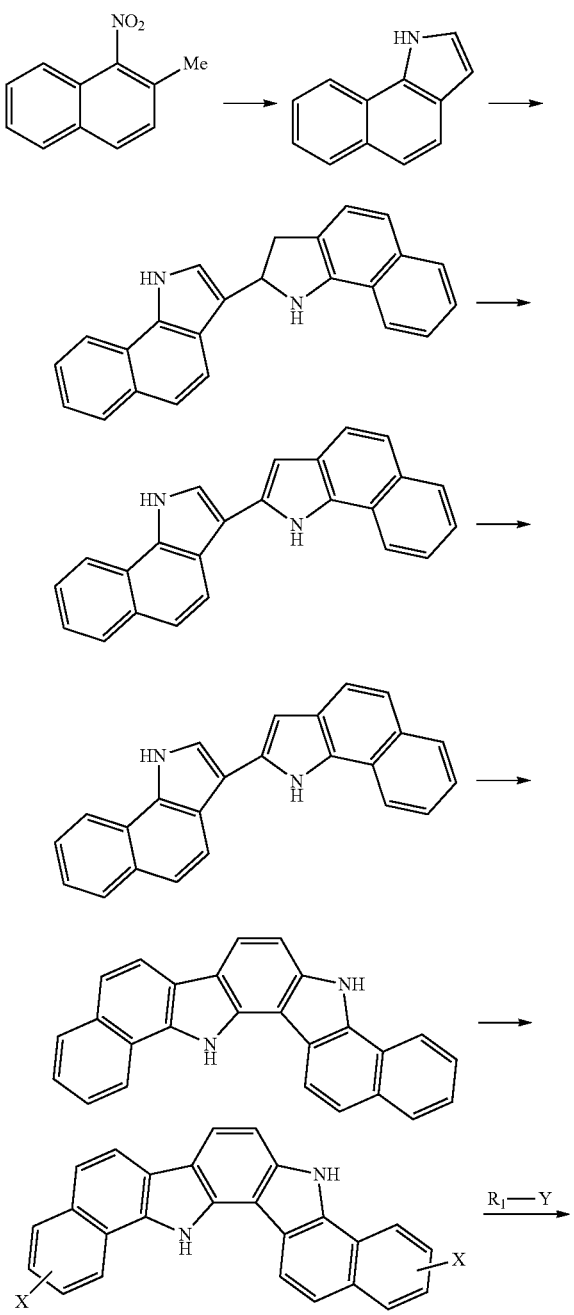

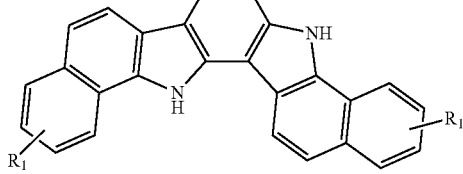

That is, the reaction formula (D) is a method involving obtaining naphthopyrrole from nitromethylnaphthalene, and then performing its dimerization reaction to obtain bisnaphthopyrrole, followed by an intramolecular cyclization reaction, the introduction of X, and a substitution reaction with $R_1$—Y.

As the substitution reaction between the compound represented by the general formula (2) and the compound represented by the general formula (3), a so-called cross-coupling reaction is preferably used, and for example, the Tamao-Kumada-Corriu reaction, the Negishi reaction, the Kosugi-Migita-Stille reaction, the Suzuki-Miyaura reaction, the Hiyama reaction, the Sonogashira reaction, the Mizoroki-Heck reaction, or the like may be used.

When the compound represented by the general formula (1) is to be obtained through the substitution reaction between the compound represented by the general formula (2) and the compound represented by the general formula (3), a target product may be obtained by performing a cross-coupling reaction selected from the above-mentioned ones as required. In this case, the reaction is performed by selecting a metal catalyst, a reaction solvent, a base, a reaction temperature, a reaction time, and the like appropriate for each reaction. After that, as required, a post-treatment operation or a purification operation, such as extraction, is performed, and thus the compound represented by the general formula (1) having a desired purity may be obtained.

Preferred specific examples of the compound represented by the general formula (1) are given using the skeleton of the general formula (4), but the compound is not limited thereto. In addition, it is also preferred to use compounds having similar substituents in the respective skeletons represented by the general formulae (5) to (18). Examples of the compound represented by the general formula (1) are given below.

(101)

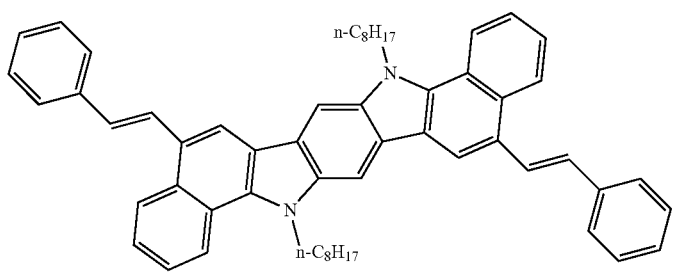

(102)
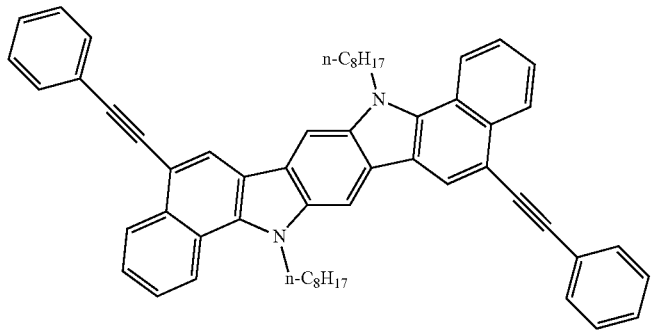
(103)
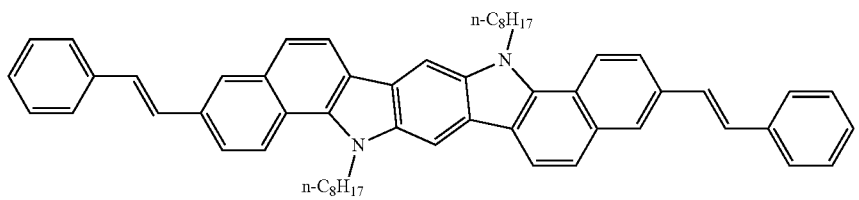
(104)
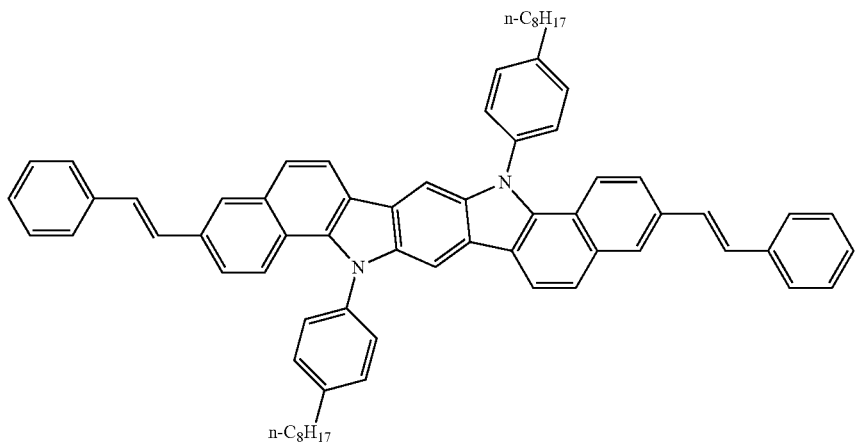
(105)
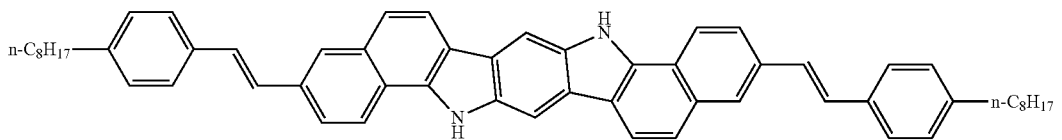
(106)
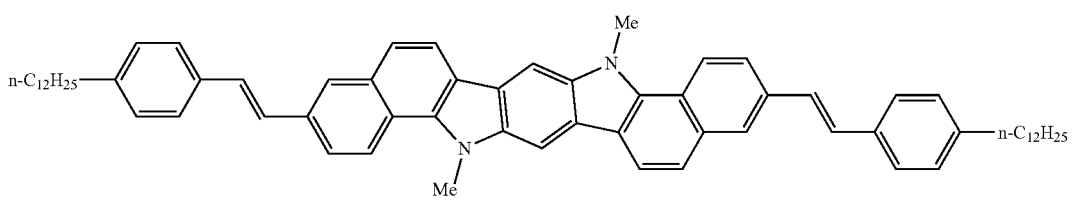
(107)
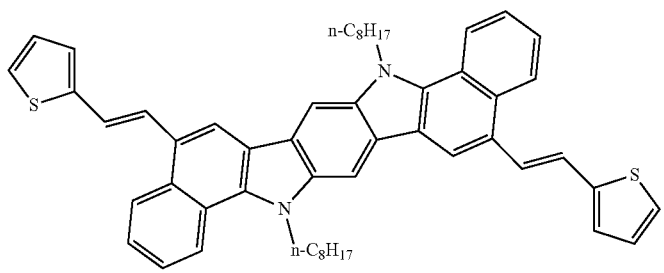

-continued
(108)
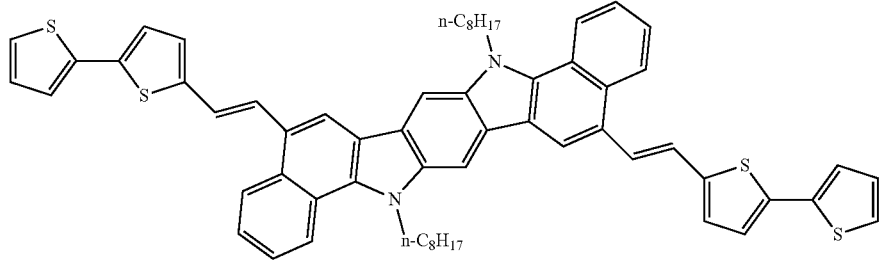
(109)
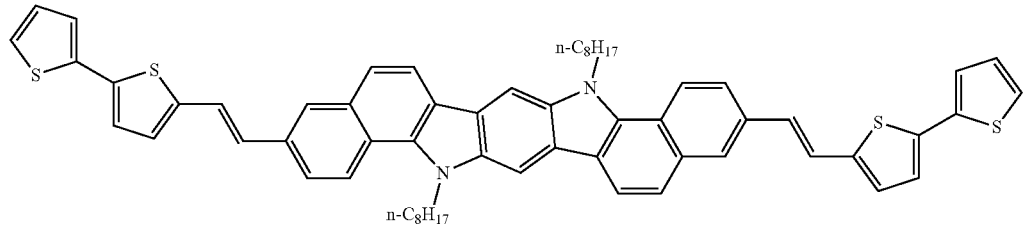
(110)
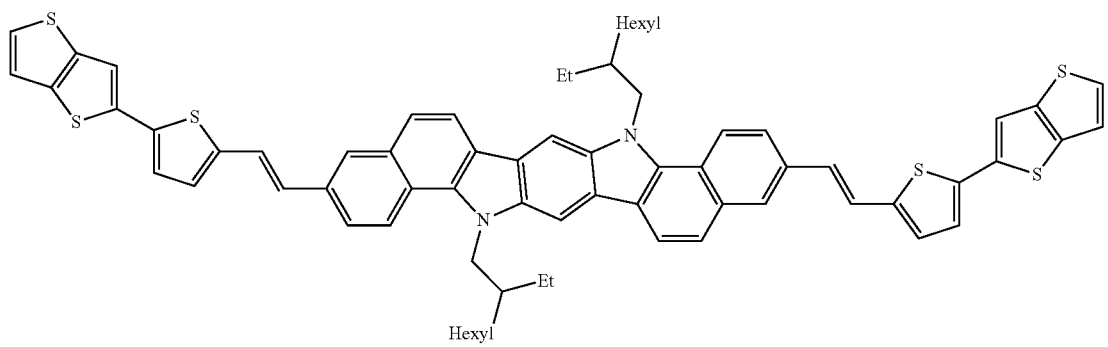
(111)
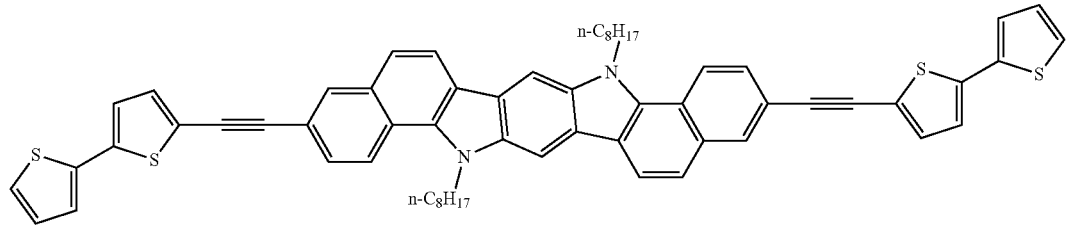
(112)
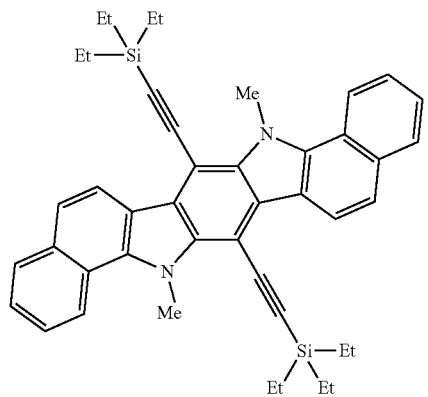
(113)
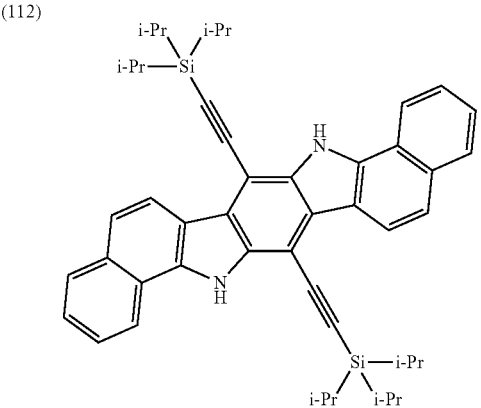

-continued
(114)
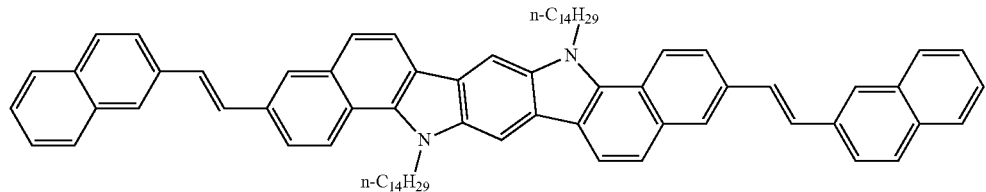
(115)
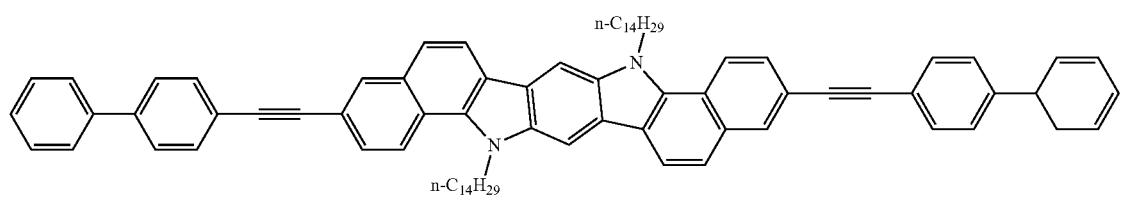
(116)
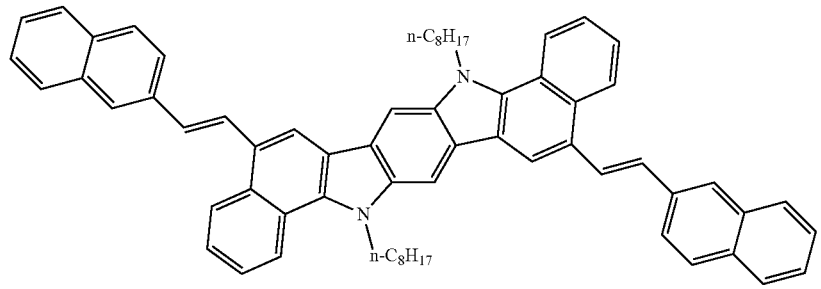
(201)
(202)
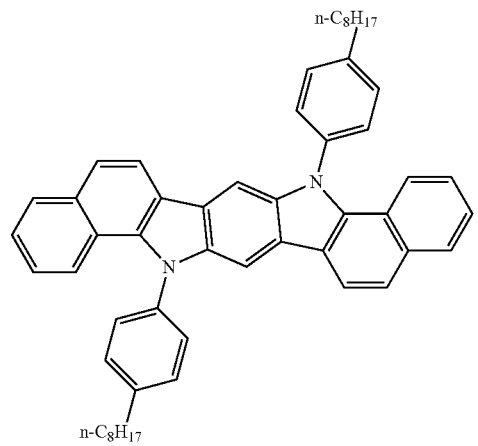
(203)
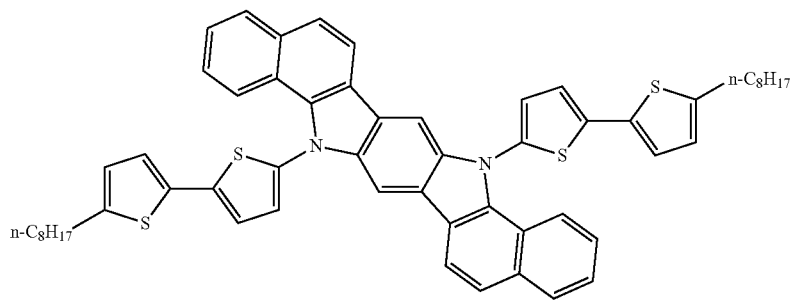

-continued
(204)
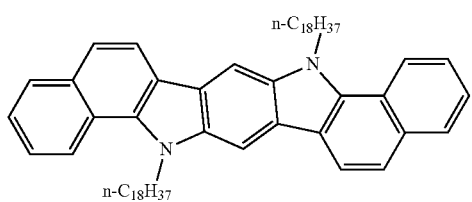
(205)
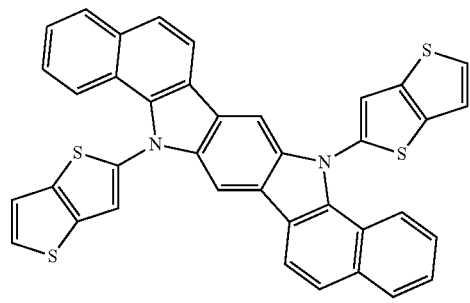
(301)
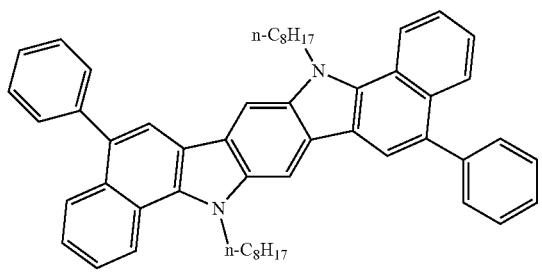
(302)
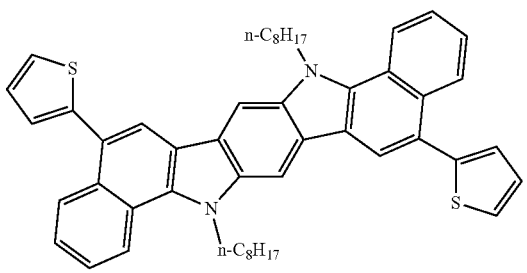
(303)
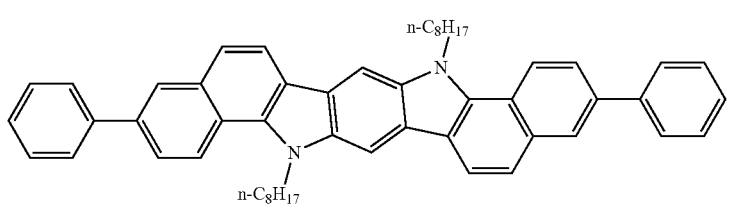
(304)
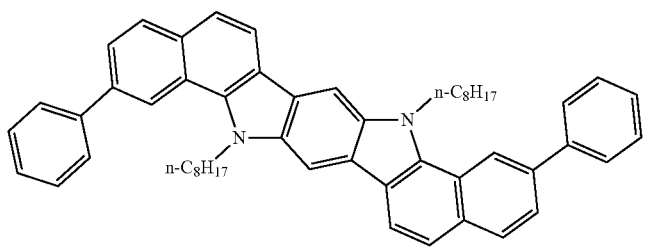
(305)
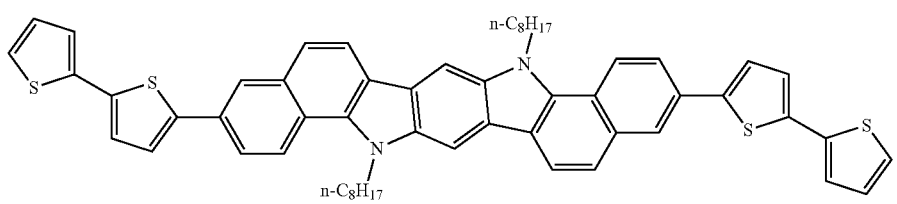
(306)
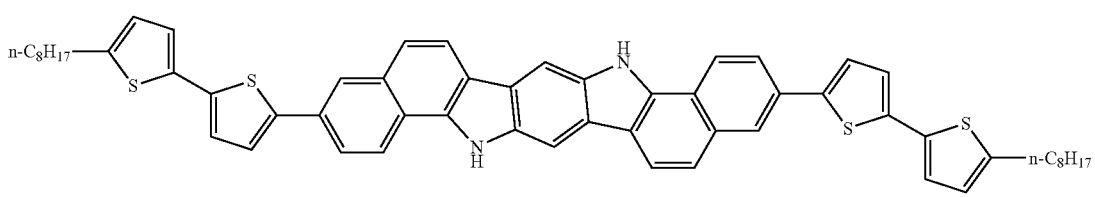

-continued
(307)
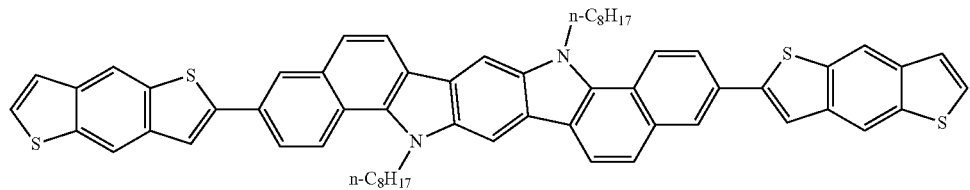
(308)
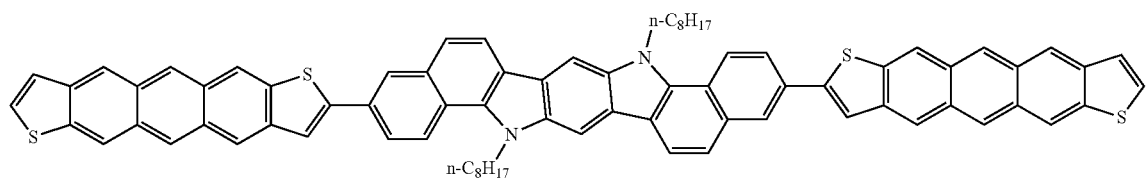
(309)
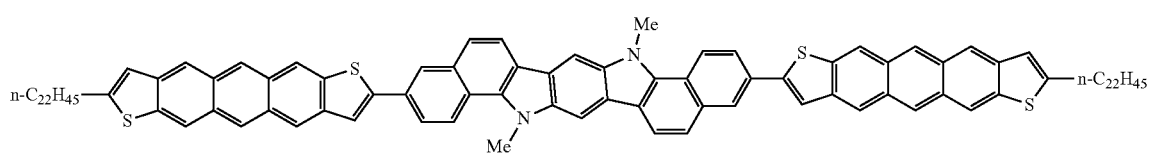
(310)
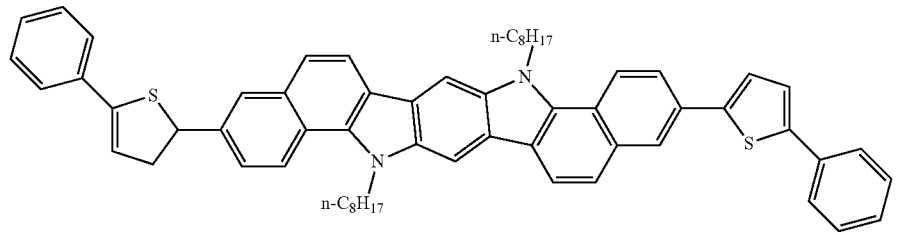
(311)
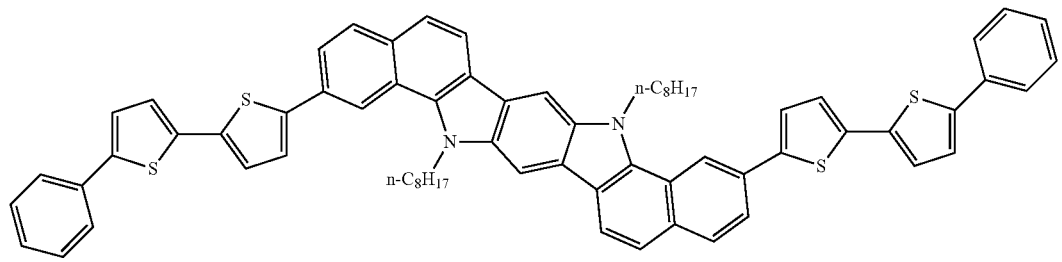
(312)
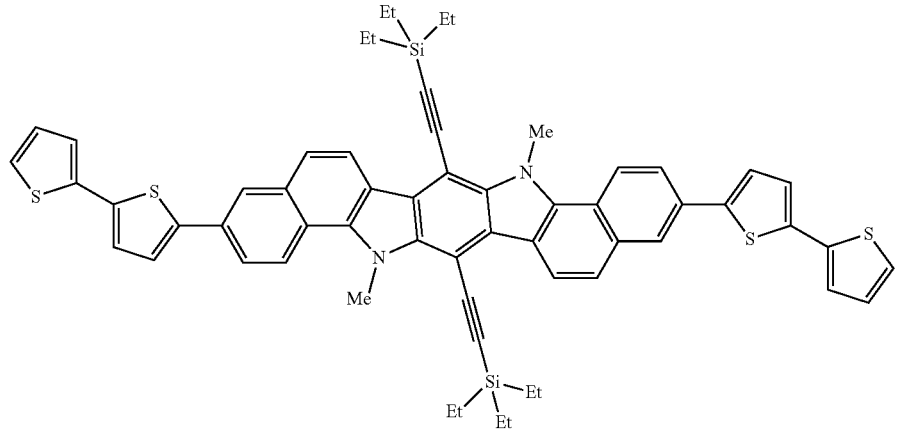

-continued
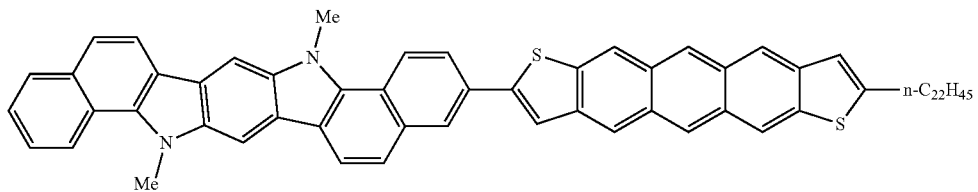
(401)
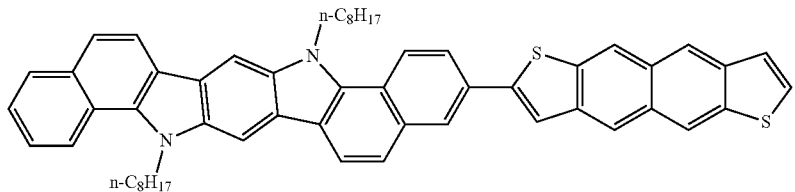
(402)
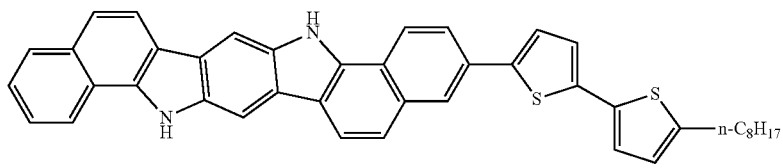
(403)
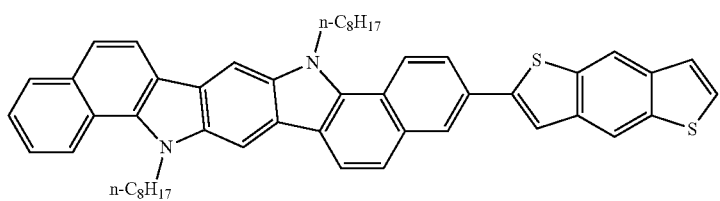
(404)
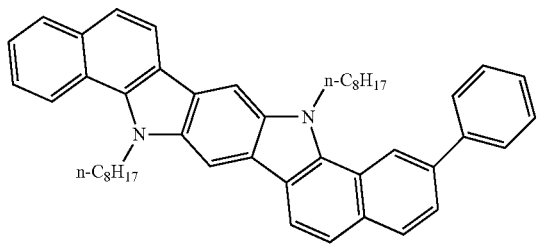
(405)
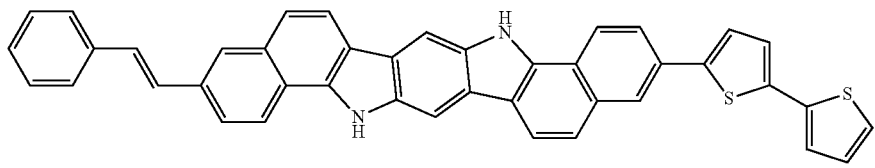
(501)
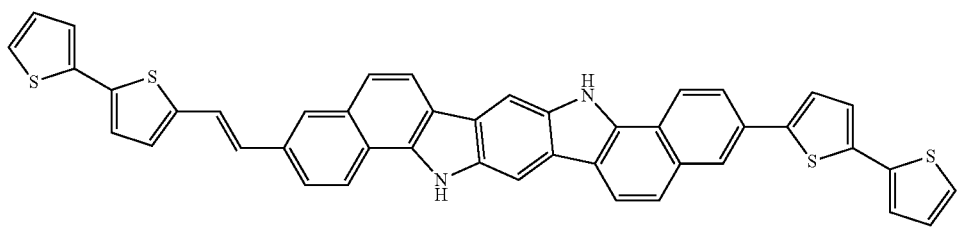
(502)
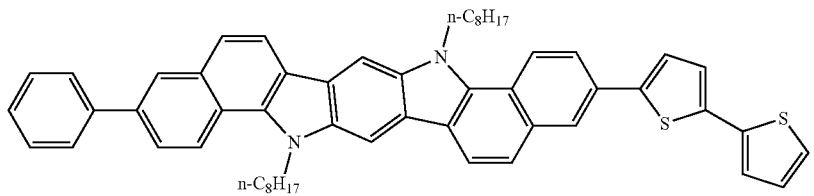
(503)

(504)
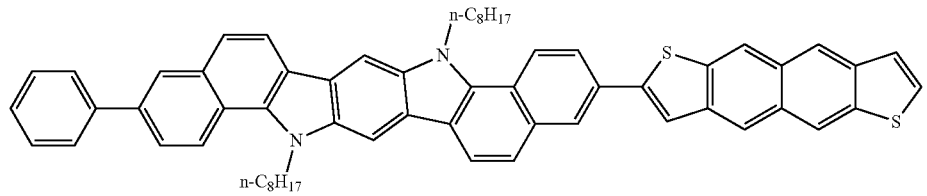
(601)
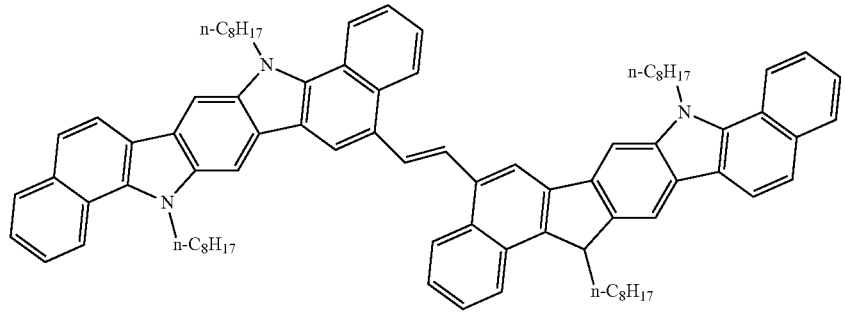
(602)
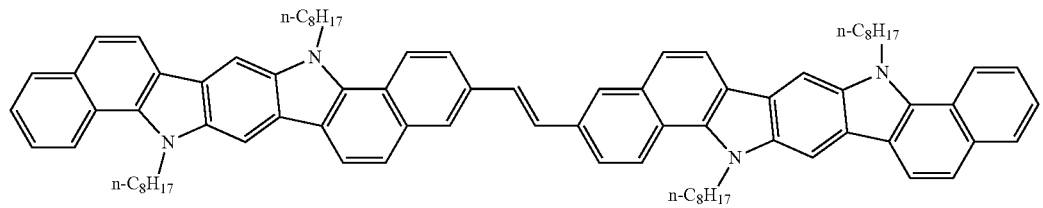
(603)
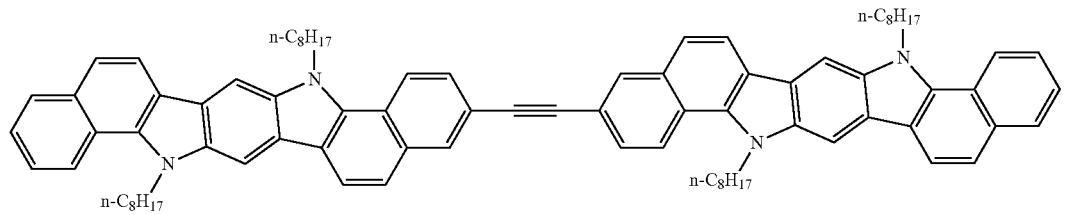
(604)
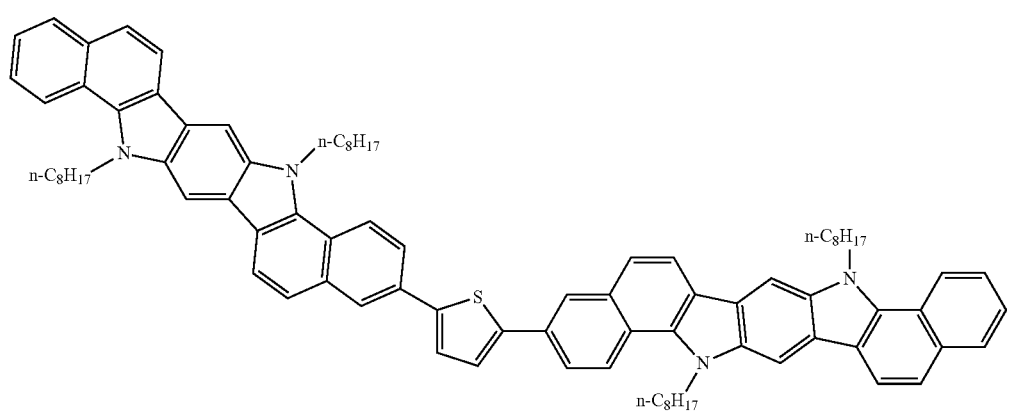
(605)
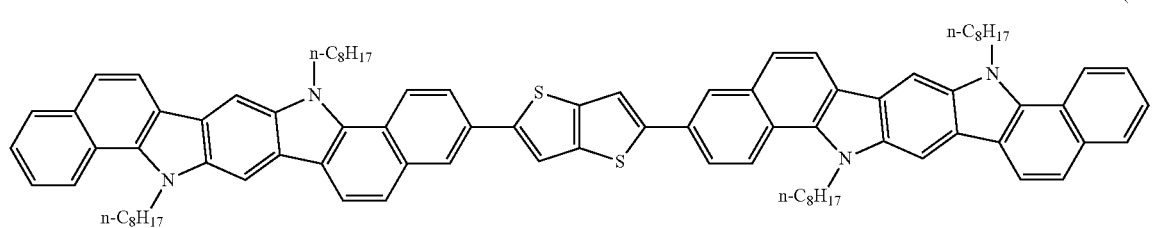

(606)
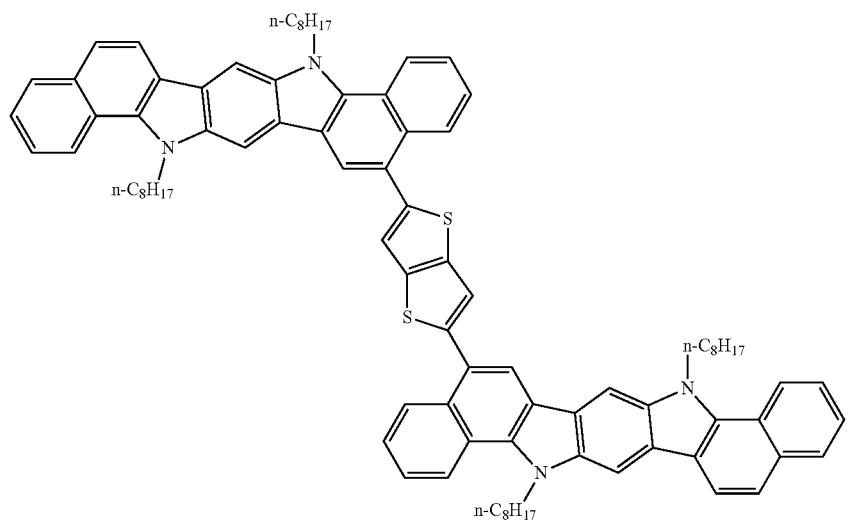
(607)
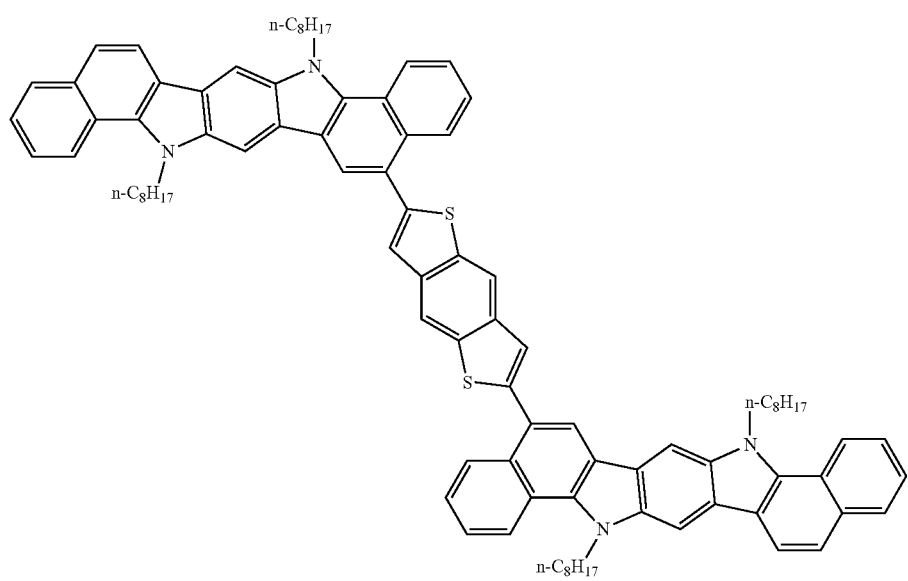
(608)
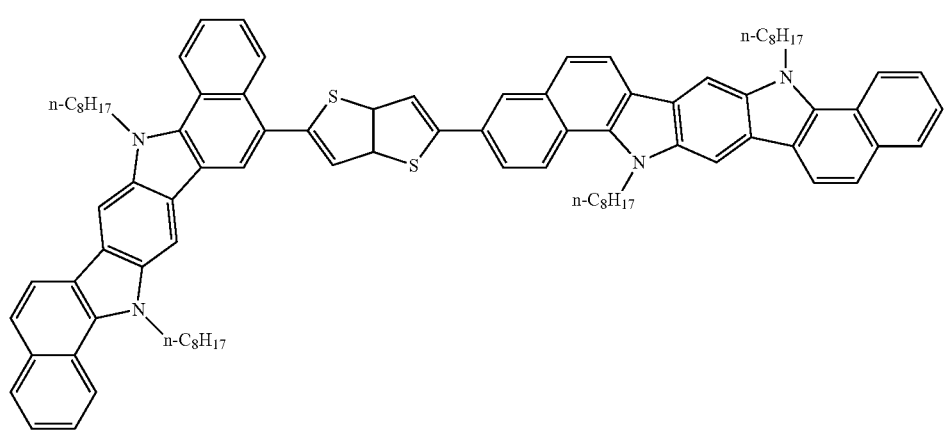

(609)

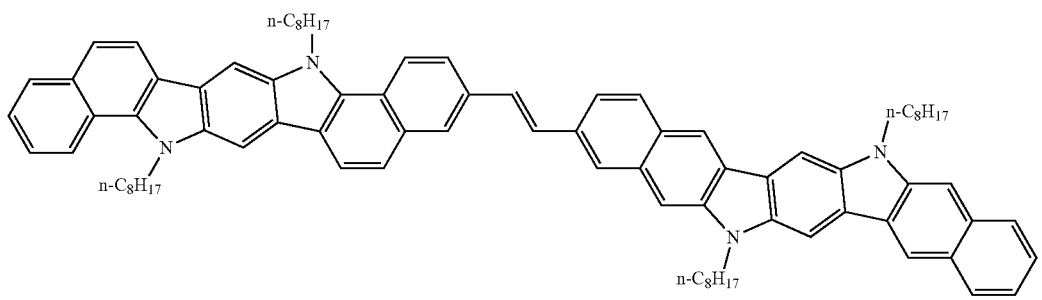

Next, an organic transistor using the organic semiconductor material for an organic transistor of the present invention is described with reference to FIG. 1 to FIG. 4.

FIG. 1, FIG. 2, FIG. 3, and FIG. 4 are each an illustration of an organic semiconductor device according to an embodiment of the present invention, and are each a schematic sectional view for illustrating the structure of an organic field-effect transistor device.

In an OTFT device illustrated in FIG. 1, a gate electrode 2 is arranged on the surface of a substrate 1, an insulating film layer 3 is formed on the gate electrode 2, a source electrode 5 and a drain electrode 6 are formed on the insulating film layer 3, and an organic semiconductor layer 4 is further formed thereon.

Figure 2:
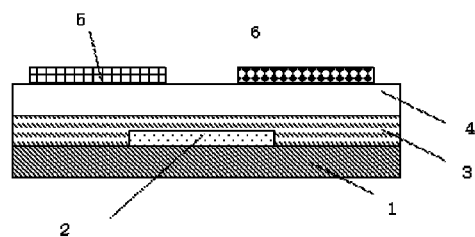
FIG. 2 is a schematic sectional view for illustrating another example of the organic field-effect transistor device.

In an OTFT device illustrated in FIG. 2, the gate electrode 2 is arranged on the surface of the substrate 1, the insulating film layer 3 is formed on the gate electrode 2, the organic semiconductor layer 4 is formed thereon, and the source electrode 5 and the drain electrode 6 are formed on the organic semiconductor layer 4.

Figure 3:
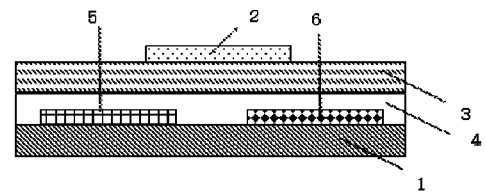
FIG. 3 is a schematic sectional view for illustrating another example of the organic field-effect transistor device.

In an OTFT device illustrated in FIG. 3, the source electrode 5 and the drain electrode 6 are formed on the surface of the substrate 1, and the gate electrode 2 is formed at the outermost surface through the intermediation of the organic semiconductor layer 4 and the insulating film layer 3.

Figure 4:
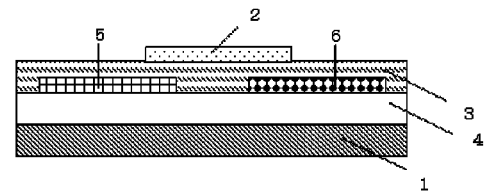
FIG. 4 is a schematic sectional view for illustrating another example of the organic field-effect transistor device.

In the case of an OTFT device illustrated in FIG. 4, in an organic semiconductor device according to the present invention, the organic semiconductor layer 4, the source electrode 5, and the drain electrode 6 are formed on the surface of the substrate 1, and the gate electrode 2 is formed at the outermost surface through the intermediation of the insulating film layer 3.

As a material to be used as the substrate 1, there are given, for example: ceramics substrates formed of glass, quartz, aluminum oxide, sapphire, silicon nitride, silicon carbide, and the like; semiconductor substrates formed of silicon, germanium, gallium arsenide, gallium phosphide, gallium nitride, and the like; and resin substrates formed of polyester such as polyethylene terephthalate or polynaphthalene terephthalate, polyethylene, polypropylene, polyvinyl alcohol, an ethylene vinyl alcohol copolymer, cyclic polyolefin, polyimide, polyamide, polystyrene, and the like. The thickness of the substrate may be set to from about 10 μm to about 2 mm. In particular, in the case of a flexible plastic substrate, the thickness may be set to, for example, from about 50 μm to about 100 μm, and in the case of a rigid substrate, such as a glass plate or a silicon wafer, the thickness may be set to from about 0.1 mm to about 2 mm.

The gate electrode 2 may be, for example, a metal thin film, a conductive polymer film, or a conductive film formed from a conductive ink or paste. Alternatively, for example, a substrate itself like heavily doped silicon may be used as the gate electrode. As a material for the gate electrode, there may be given, for example, aluminum, copper, stainless steel, gold, chromium, an n-doped or p-doped silicon, an indium tin oxide, a conductive polymer such as polystyrenesulfonic acid-doped poly(3,4-ethylenedioxythiophene), a conductive ink/paste containing carbon black/graphite, and one obtained by dispersing colloidal silver into a polymer binder.

The gate electrode 2 may be produced by using, for example, vacuum vapor deposition, sputtering of a metal or a conductive metal oxide, or spin coating, inkjet, spraying, coating, or casting of a conductive polymer solution or a conductive ink. The thickness of the gate electrode 2 preferably falls within, for example, the range of from about 10 nm to about 10 μm.

The insulating film layer 3 may be generally an inorganic material film or an organic polymer film. As an inorganic material suitable as the insulating film layer 3, there may be given, for example, silicon oxide, silicon nitride, aluminum oxide, barium titanate, and barium zirconium titanate. As an organic compound suitable as the insulating film layer 3, there are given, for example, polyester, polycarbonate, poly(vinylphenol), polyimide, polystyrene, poly(methacrylate), poly(acrylate), and an epoxy resin. In addition, an insulating layer film obtained by dispersing an inorganic material in an organic polymer may be used. The thickness of the insulating film layer varies depending on the dielectric constant of an insulating material to be used, but is, for example, from about 10 nm to about 10 μm.

As means for forming the insulating film layer, there are given, for example: a dry film-forming method, such as a vacuum deposition method, a CVD method, a sputtering method, and a laser deposition method; and a wet film-forming method, such as a spin coating method, a blade coating method, a screen printing, inkjet printing, and a stamp method, and the means may be used depending on the material.

The source electrode 5 and the drain electrode 6 may each be formed from a material which provides low-resistance ohmic contact to the organic semiconductor layer 4 to be described later. As materials preferred as the source electrode 5 and the drain electrode 6, those given as materials preferred for the gate electrode 2 may be used, and examples thereof include gold, nickel, aluminum, platinum, a conductive polymer, and a conductive ink. The thickness of each of the source electrode 5 and the drain electrode 6 is typically, for example, from about 40 nm to about 10 μm, and the thickness is more preferably from about 10 nm to about 1 μm.

As means for forming each of the source electrode 5 and the drain electrode 6, for example, there are given a vacuum deposition method, a sputtering method, an application method, a thermal transfer method, a printing method, and a sol-gel method. At the time of film formation or after film formation, patterning is preferably performed as required. As a method for the patterning, for example, there is given a photolithography method involving a combination of patterning and etching of a photoresist. In addition, the patterning may also be performed by utilizing, for example, a printing method, such as inkjet printing, screen printing, or offset printing, a soft lithography method such as a microcontact printing method, or a method involving a combination of a plurality of these methods.

As means for forming the organic semiconductor layer 4, for example, there are given: a dry film-forming method, such as a vacuum deposition method, a CVD method, a sputtering method, or a laser deposition method; and a wet film-forming method, which involves applying a solution or a dispersion onto a substrate, and then removing a solvent or a dispersion medium to form a thin film. Of those, a wet film-forming method is preferably used. Examples of the wet film-forming method may include a spin coating method, a blade coating method, screen printing, inkjet printing, and a stamp method. For example, when the spin coating method is used, the organic semiconductor material of the present invention is dissolved in an appropriate solvent in which the organic semiconductor material has solubility, to thereby prepare a solution having a concentration of from 0.01 wt % to 10 wt %, and then the solution of the organic semiconductor material is dropped onto the insulating film layer 3 formed on the substrate 1, followed by rotating the resultant at from 500 to 6,000 rpm for from 5 sec to 120 sec. The solvent is selected depending on the solubility of the organic semiconductor material in each solvent and film quality after film formation, and there may be used a solvent selected from, for example: water; alcohols typified by methanol; aromatic hydrocarbons typified by toluene; aliphatic hydrocarbons typified by hexane, cyclohexane, and the like; organic nitro compounds such as nitromethane and nitrobenzene; cyclic ether compounds such as tetrahydrofuran and dioxane; nitrile-based compounds such as acetonitrile and benzonitrile; ketones such as acetone and methyl ethyl ketone; esters such as ethyl acetate; and aprotic polar solvents typified by dimethyl sulfoxide, dimethylacetamide, sulfolane, N-methylpyrrolidone, dimethylimidazolidinone, and the like. In addition, two or more kinds of those solvents may be used in combination.

An organic field-effect transistor device using the organic semiconductor material of the present invention may be produced by the method described above. In the obtained organic field-effect transistor device, the organic semiconductor layer forms a channel region, and on-off operation is performed through the control of a current flowing between the source electrode and the drain electrode based on a voltage to be applied to the gate electrode.

The organic semiconductor material for an organic transistor of the present invention has a high charge mobility, solvent solubility, oxidation stability, and satisfactory film formability, and an organic transistor using the material also exhibits high characteristics. The incorporation of the organic transistor of the present invention enables the device to find applications in information tags, large-area sensors such as electronic artificial skin sheets and sheet-type scanners, and displays such as liquid crystal displays, electronic paper, and organic EL panels.

EXAMPLES

The present invention is described in more detail by way of Examples below. It should be appreciated that the present invention is not limited to these Examples and may be carried out in various forms as long as the various forms do not deviate from the gist of the present invention. It should be noted that numbers of compounds correspond to the numbers described in the chemical formulae.

Example 1

Synthesis Example of Compound (101)

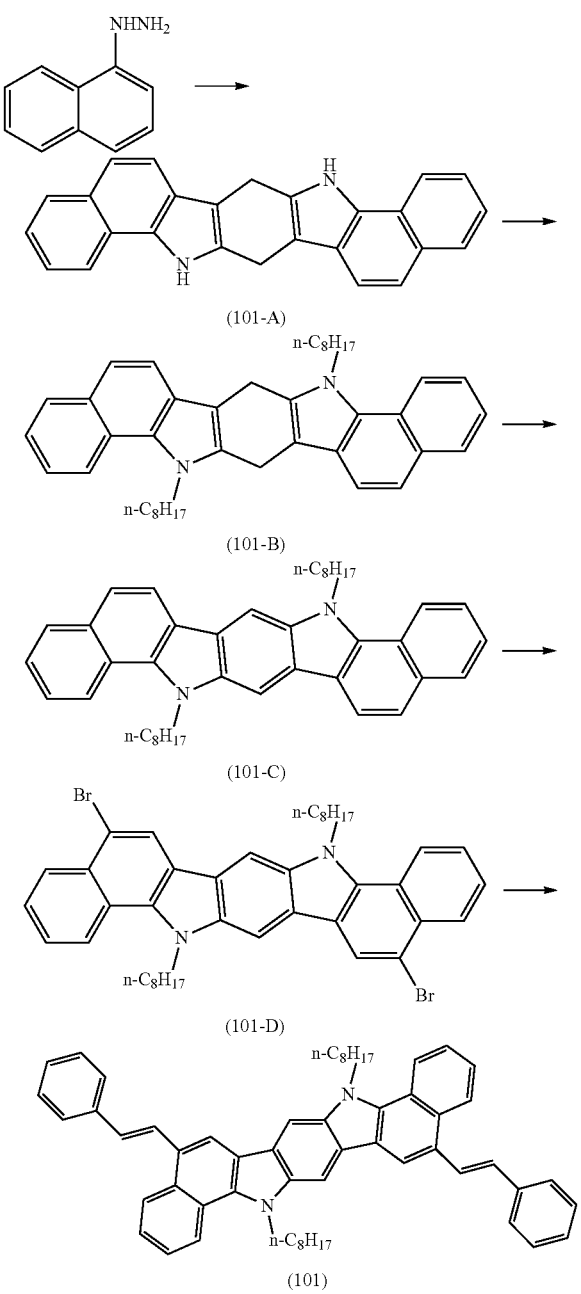

In a 3,000-ml three-necked flask equipped with a reflux condenser and a mechanical stirrer, to 1-naphthylhydrazine hydrochloride (108.7 g, 558.4 mmol) and 1,4-cyclohexanedione (25.0 g, 223.4 mmol), 1,200 mL of acetic acid was added, and the mixture was stirred under a stream of argon. Sulfuric acid (165 mL, 3,095 mmol) was added dropwise at 30° C. or less. After that, the mixture was stirred at 110° C. After 2 hr, the reaction liquid was charged into 2.4 L of cold water, followed by stirring for 30 min. The resultant was filtered to provide a brown solid. The resultant solid was stirred under reflux with 500 mL of methanol for 30 min, and then a precipitate was taken by filtration. To the solid, 500 mL of THF was added, and the mixture was stirred under heating to reflux for 30 min, followed by separation by filtration. The resultant filtrate was brought to dryness to provide 8.9 g of Compound (101-A) as a reddish brown solid.

In a three-necked flask, to 10.0 g of Compound (101-A), 240 mL of DMF was added, and the mixture was stirred under a stream of argon at room temperature for 30 min. 2.47 g of 60% sodium hydride was washed by being decanted twice with 50 mL of hexane and was prepared into 50 mL of a hexane suspension. The suspension was added dropwise, and the mixture was stirred at room temperature for 30 min. To the reaction liquid, 11.1 mL of iodooctane was added dropwise, and then the mixture was stirred at room temperature. After 18 hr, the reaction liquid was dropped into 1,000 mL of water, and the mixture was stirred. A precipitate was taken by filtration, and then dried to provide 11.8 g of Compound (101-B) as a yellow solid.

In a three-necked flask, to 11.8 g of Compound (101-B), 1,100 mL of dichloromethane was added, and the mixture was stirred at room temperature. When the solution became homogeneous, 4.54 g of DDQ was added, and the mixture was stirred. After 2 hr, the resultant was filtered to remove insoluble matter. The filtrate was concentrated to provide 11.75 g of a concentrate. To the concentrate, 500 mL of methanol was added, and the mixture was stirred for 30 min at room temperature. After that, the resultant was filtered and dried to provide 10.5 g of Compound (101-C) as a yellow-green solid.

Figure 5:
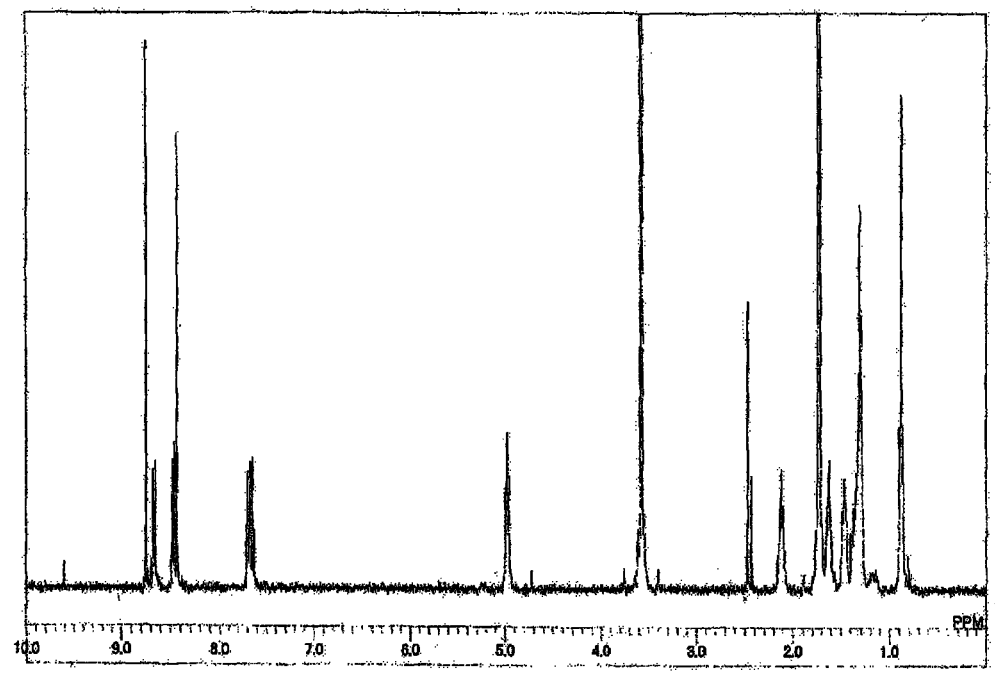
FIG. 5 is an NMR chart of Intermediate 101-D.

In a three-necked flask, to 1.50 g of Compound (101-C), 150 mL of THF was added, and the mixture was stirred under a stream of argon at room temperature for 10 min. 0.459 g of N-bromosuccinimide was added and the mixture was stirred at room temperature. After 30 min, 0.229 g of N-bromosuccinimide was added and the mixture was stirred. After 30 min, 0.115 g of N-bromosuccinimide was added and the mixture was stirred. After 13 hr, 0.057 g of N-bromosuccinimide was further added and the mixture was stirred. Further 3 hr after that, 0.0285 g of N-bromosuccinimide was added and the mixture was stirred. 1 hr after that, 0.0143 g of N-bromosuccinimide was added and the mixture was stirred. After 1 hr, the resultant was charged into 300 mL of water. The mixture was stirred for about 1 hr, filtered, and dried to provide 1.88 g of a yellow solid. As a result of NMR analysis and MS analysis, the yellow solid was found to be Compound (101-D). The NMR measurement result is shown in FIG. 5. FDMS: m/z 738.

Figure 6:
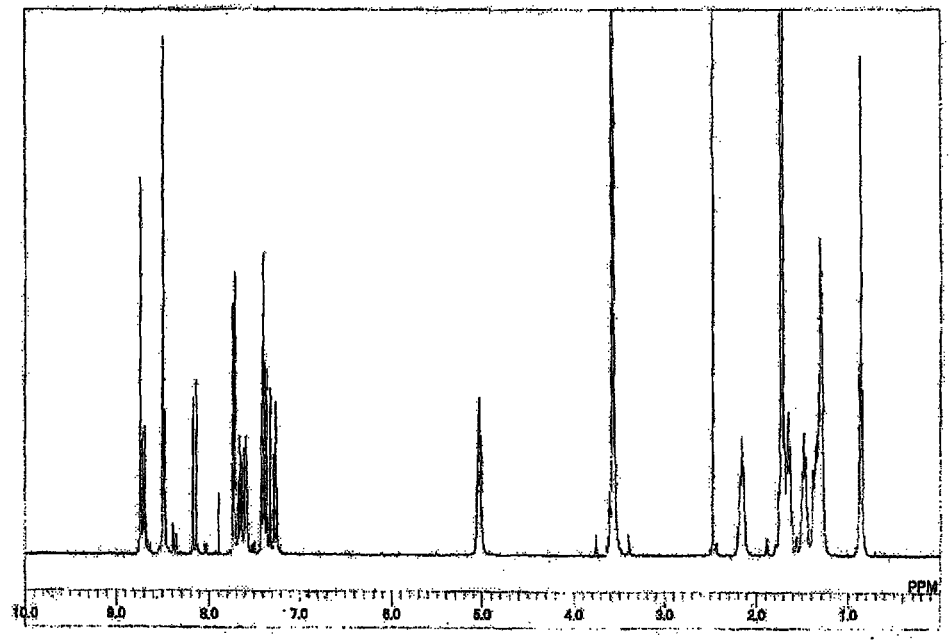
FIG. 6 is an NMR chart of Compound 101.

In a flask equipped with a reflux condenser, 3.0 g of Compound (101-D), 1.27 g of styrene, 0.106 g of triphenylphosphine, 60 mL of DMAc, and 60 mL of triethylamine were added, and the mixture was stirred under a stream of argon at room temperature for 10 min. 0.469 g of tetrakistriphenylphosphinepalladium(0) was added, and then the mixture was stirred at 80° C. After 18 hr, 50 mL of water was added, and the mixture was stirred for 1 hr, and then a precipitate was taken by filtration. To the product taken by filtration, 50 mL of methanol was added and the mixture was refluxed. After 30 min, the resultant was allowed to cool, filtered, and dried to provide 2.9 g of a yellow solid. As a result of NMR analysis and MS analysis, the yellow solid was found to be Compound (101). The NMR measurement result is shown in FIG. 6. FDMS: m/z 784.

Example 2

The characteristics of the organic semiconductor material for an organic transistor of the present invention were evaluated by producing an organic field-effect transistor having a construction illustrated in FIG. 2. First, a silicon wafer (n-doped) having a thermally grown silicon oxide layer having a thickness of about 300 nm was washed with a solution of sulfuric acid in hydrogen peroxide water and boiled with isopropyl alcohol, followed by drying. A solution (2 wt %) of Compound (101) in chlorobenzene was formed into a film on the resultant silicon wafer (n-doped) having a thermally grown silicon oxide layer by a spin coating method, followed by heat treatment at 80° C. to form a thin film of Compound (101) having a thickness of 50 nm. Further, gold was deposited onto the surface of the film using a mask to form a source electrode and a drain electrode. The source electrode and the drain electrode had a width of 100 µm and a thickness of 200 nm, and an organic transistor having a channel width of W=2 mm and a channel length of L=50 µm was produced.

A voltage of from −10 V to −100 V was applied between the source electrode and drain electrode of the resultant organic transistor, and then a gate voltage was changed in the range of from −30 V to −80 V to determine its voltage-current curve at a temperature of 25° C., followed by the evaluation of the organic transistor for its transistor characteristics. A field-effect mobility (µ) was calculated with the following equation (I) representing a drain current $I_d$.

$$I_d = (W/2L)\mu C_i (V_g - V_t)^2 \quad (I)$$

In the equation (I), L represents the channel length and W represents the channel width. In addition, $C_i$ represents the capacity of an insulating layer per unit area, $V_g$ represents the gate voltage, and $V_t$ represents a threshold voltage. A non-off ratio was calculated from a ratio between the maximum and minimum drain current values ($I_d$).

The mobility and the on-off ratio were found to be $8.8 \times 10^{-1}$ cm$^2$/Vs and $10^4$, respectively.

Example 3

Compound (116) was obtained by performing operations in the same manner as in Example 1 except that 2-vinylnaphthalene was used instead of styrene. FDMS: m/z 884.

Example 4

Operations were performed in the same manner as in Example 2 except that Compound (116) was used instead of Compound (101). As a result, the following characteristic values were obtained.

Mobility; $6.8 \times 10^{-1}$ cm$^2$/Vs, on-off ratio; $10^5$

Example 5

Operations were performed in the same manner as in Example 2 except that Compounds (102), (103), (107), (109), and (113) were used instead of Compound (101). The results are shown in Table 1.

TABLE 1

| Compound | Mobility (cm²/Vs) | On-off ratio |
|---|---|---|
| 102 | $3.8 \times 10^{-1}$ | $10^5$ |
| 103 | $4.6 \times 10^{-1}$ | $10^4$ |
| 107 | $2.7 \times 10^{-1}$ | $10^6$ |
| 109 | $8.5 \times 10^{-1}$ | $10^5$ |
| 113 | 1.2 | $10^5$ |

Comparative Example 1

An organic transistor was produced by performing the same operations as those of Example 2 except that a solution (2 wt %) of 5,11-dioctylindolo[3,2b]carbazole in chlorobenzene was used instead of the solution (2 wt %) of Compound (101) in chlorobenzene. The resultant device was evaluated in the same manner as in Example 2 and found to have a mobility of $1.1 \times 10^{-4}$ cm²/Vs and an on-off ratio of $10^5$.

As described above, on the basis of the comparison of Examples 2, 3, 4, and 5 to Comparative Example 1, it was revealed that the organic transistors each using the organic semiconductor material for an organic transistor represented by the formula (1) had high characteristics.

The invention claimed is:

1. An organic semiconductor material for an organic transistor, comprising a compound represented by the following general formula (1):

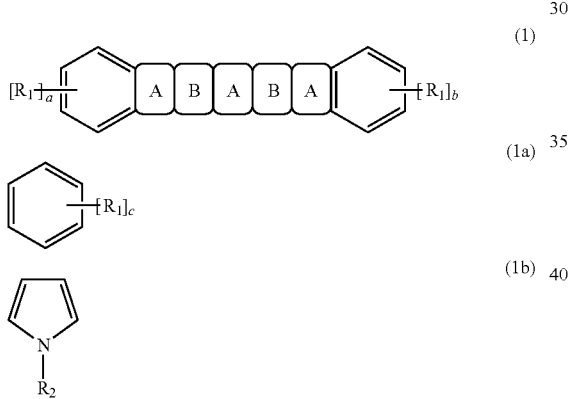

wherein,
rings A each represent an aromatic ring represented by the formula (1 a) to be fused to adjacent rings at arbitrary positions;
rings B each represent a heterocycle represented by the formula (1 b) to be fused to adjacent rings at arbitrary positions;
$R_1$'s each independently represent a group selected from the group consisting of an alkenyl group having 2 to 50 carbon atoms, and an alkynyl group having 2 to 50 carbon atoms;
$R_2$'s each independently represent a group selected from the group consisting of hydrogen, an alkyl group having 1 to 30 carbon atoms, an aromatic hydrocarbon group having 6 to 50 carbon atoms, and a heteroaromatic group having 3 to 50 carbon atoms; and
a, b, and c each represent an integer of 0 or more satisfying a relationship of a+b+c>1.

2. A production method for the organic semiconductor material for an organic transistor of claim 1, the production method comprising allowing a compound represented by the following general formula (2) and a compound represented by the following general formula (3) to react with each other to produce a compound in which X in the general formula (2) is substituted with $R_1$:

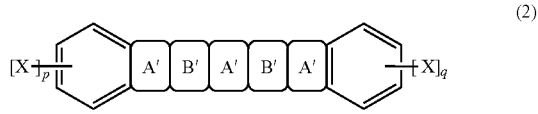

wherein,
rings A' each represent an aromatic ring represented by the formula (2a) to be fused to adjacent rings at arbitrary positions;
rings B' each represent a heterocycle represented by the formula (2b) to be fused to adjacent rings at arbitrary positions;
X represents any one of a halogen atom, a $CF_3SO_3$ group, a trialkylsilyl group, an organoboron group, an organotin group, a magnesium halide group, and a zinc halide group; and
p, q, and r each represent an integer of 0 or more satisfying a relationship of p+q+r>1;

wherein,
$R_1$ has the same meaning as $R_1$ in the general formula (1); and
Y represents a group which reacts with X in the general formula (2) to leave as X—Y and to allow substitution of X with $R_1$.

3. An organic thin-film transistor, comprising a semiconductor layer using the organic semiconductor material of claim 1.

* * * * *